US 6,649,041 B2

(12) United States Patent
Hashimoto et al.

(10) Patent No.: US 6,649,041 B2
(45) Date of Patent: Nov. 18, 2003

(54) DETERIORATION DETECTOR FOR EXHAUST GAS SENSOR AND METHOD OF DETECTING DETERIORATION

(75) Inventors: Kohji Hashimoto, Tokyo (JP); Masaharu Yuhara, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 221 days.

(21) Appl. No.: 09/858,721

(22) Filed: May 17, 2001

(65) Prior Publication Data

US 2002/0060150 A1 May 23, 2002

(30) Foreign Application Priority Data

Nov. 22, 2000 (JP) ...................... P2000-355334

(51) Int. Cl.[7] .............................................. G01N 27/41
(52) U.S. Cl. .................. 205/785; 204/401; 204/406; 204/424; 123/697; 701/109
(58) Field of Search ................. 204/401, 406, 204/408, 424; 205/775, 785; 123/690, 697; 701/109

(56) References Cited

U.S. PATENT DOCUMENTS

| | | | |
|---|---|---|---|
| 5,709,198 A | * | 1/1998 | Sagisaka et al. ............ 123/684 |
| 5,852,228 A | * | 12/1998 | Yamashita et al. .......... 73/23.32 |
| 6,084,418 A | | 7/2000 | Takami et al. |
| 6,131,446 A | | 10/2000 | Schnaibel et al. |
| 6,279,377 B1 | * | 8/2001 | Cao .......................... 73/23.31 |

FOREIGN PATENT DOCUMENTS

| | | |
|---|---|---|
| JP | 8-121221 | 5/1996 |
| JP | 8-313477 | 11/1996 |

* cited by examiner

*Primary Examiner*—Kaj K. Olsen
(74) *Attorney, Agent, or Firm*—Sughrue Mion, PLLC

(57) ABSTRACT

The invention provides a deterioration detector for an exhaust gas sensor capable of detecting an amount of change with age of an internal resistance and conducting deterioration judgment taking into consideration fluctuation between products and temperature dependency of the internal resistance of the exhaust gas sensor.

The deterioration detector for an exhaust gas sensor computes and stores an initial internal resistance of an exhaust gas sensor (5) and an electric heater (4) within a period of time determined by a data collection period judgement apparatus (109), learns and stores a correlation between the initial internal resistances of the exhaust gas sensor and the electric heater, after a data collection period of time, by an abnormal condition judgement apparatus (115), computes and stores a current internal resistance of the exhaust gas sensor (5) and the electric heater (4), and detects an abnormal condition in the case of the current internal resistance being greatly varied over a predetermined permissible value by comparing the current internal resistance of the exhaust gas sensor and the electric heater with the initial internal resistance learned and stored.

6 Claims, 2 Drawing Sheets

DETERIORATION DETECTOR FOR EXHAUST GAS SENSOR AND METHOD OF DETECTING DETERIORATION

BACKGROUND OF THE INVENTION

1. Technical Field

The present invention relates to a deterioration detector for an exhaust gas sensor to detect a concentration of oxygen contained in exhaust gas discharged from an internal combustion engine and, more particularly, to a deterioration detector for an exhaust gas sensor capable of totally detecting deterioration of an exhaust gas sensor and abnormal condition of an electric heater wherein an exhaust gas sensor used in combination with an electric heater thereby improving accuracy in detection of an exhaust gas is employed. The invention relates also to a method for detecting the deterioration.

2. Background Art

A conventional technique has been well known in which a concentration of oxygen contained in exhaust gas discharged from an internal combustion engine is detected, feedback control of an air/fuel ratio of fluid mixture supplied to the internal combustion engine is conducted and exhaust gas is purified and a rate of fuel combustion is improved.

In order to conduct the feedback control, it is necessary to keep the exhaust gas sensor within an activating region and stabilize detection characteristic of the oxygen concentration. Therefore, a ceramic heater incorporated in the exhaust gas sensor is controlled in terms of energizing and the exhaust gas sensor is kept at a constant temperature.

As to detection of a temperature of an exhaust gas sensor to serve as a basic art, for example as disclosed in the Japanese Patent Publication (unexamined) No. 292364/1997 and the Japanese Patent Publication (unexamined) No. 313477/1996, a method is employed wherein an internal resistance of an exhaust gas sensor is measured and temperature of the exhaust gas sensor itself is detected using the internal resistance of the exhaust gas sensor as a reference. Additionally, as disclosed in the Japanese patent Publication (unexamined) No. 313476/1996 and the Japanese patent publication (unexamined) No. 4502/1997, such a method is employed as to detect a peripheral temperature of an exhaust gas sensor by measuring a resistance value of an electric heater incorporated in the exhaust gas sensor.

As for a method of detecting deterioration of an exhaust gas sensor, as disclosed in the Japanese Patent Publication (unexamined) No. 331700/1998 and the Japanese Patent Publication (unexamined) No. 121221/1996, means for changing intentionally operating condition of an internal combustion engine and observing reaction change speed and output variance waveform of a detection output of an exhaust gas sensor in response to the change of operating condition of the internal combustion engine.

In case of employing such a conventional art as described above, a problem exists in that large-scaled means for changing operating condition of the internal combustion engine has been required just for detecting the deterioration of the exhaust gas sensor. A further problem exists in that abnormal condition of the electric heater integrated with the exhaust gas sensor cannot be detected.

SUMMARY OF THE INVENTION

The present invention was made to solve the above-discussed problems, and has an object of providing a deterioration detector for an exhaust gas sensor and a method for detecting deterioration wherein total deterioration detection of an exhaust gas sensor including deterioration of an electric heater is easily performed simply by utilizing means for observing change with age in internal resistance of an exhaust gas sensor together with detection of abnormal condition of the electric heater.

The present invention is to provide a simple deterioration detector for an exhaust gas sensor and a method for detecting deterioration wherein change with age in internal resistance is extracted taking into consideration fluctuation between products and temperature dependency of an exhaust gas sensor and an electric heater.

A deterioration detector for an exhaust gas sensor according to the present invention that is mounted on an exhaust pipe of an internal combustion engine for an automobile and is arranged so as to control a temperature by an electric heater thereby detecting deterioration of the exhaust gas sensor comprises:

initial internal resistance correlation learning storage means for sequentially sampling, comparing, computing and storing an initial internal resistance of said exhaust gas sensor and said electric heater;

data collection period judgement means for determining a period of sampling said initial internal resistance; and abnormal condition judgment means for computing and storing a current internal resistance of said exhaust gas sensor and said electric heater after a predetermined period of time of an operation start of said internal combustion engine for an automobile, for judging that said current internal resistance has varied greatly over a predetermined permissible value by comparing said current internal resistance with said initial internal resistance, thereby conducting a processing for the abnormal condition.

As a result of such an arrangement, deterioration of the exhaust gas sensor as well as the abnormal condition of the electric heater can be detected, and a timing of replacement and repair of an integrally formed exhaust gas sensor and electric heater can be known.

In the deterioration detector for an exhaust gas sensor of above arrangement according to the invention, it is preferable that, in the case that an initial internal resistance of the exhaust gas sensor and the electric heater which is newly sampled, computed and measured is closely analogous to the initial internal resistance already learned and stored, the initial internal resistance correlation learning storage means averages the value of said initial internal resistance newly sampled and that of said initial internal resistance learned and stored, and stores the averaged value for renewal.

As a result of such arrangement, any useless proximate information is not stored, a memory capacity can be reduced, and an amount of information to be referenced and read out is eliminated, making it possible to perform a high-speed processing.

Further, in a deterioration detector for an exhaust gas sensor of above arrangement according to the invention, it is preferable that the data collection period judgement means judges a completion of the data collection period based on the fact that a sampling number of the initial internal resistance of the exhaust gas sensor or the electric heater stored in initial internal resistance correlation learning storage means, is not less than a predetermined number and a correlation coefficient not less than a predetermined value is surely obtained.

As a result of such arrangement, even if there might be any fluctuation of the internal resistance of the exhaust gas sensor or the electric heater between one sensor or heater and another, learning and storing an initial value of an actually utilized sensor or heater enables to detect a later change, and a data collection period can be determined by confirming whether or not a sufficient number of data could be obtained.

Further, in a deterioration detector for an exhaust gas sensor of above arrangement according to the invention, it is preferable that the abnormal condition judgment means comprises computing interpolation means for computing, on the assumption that either one of the current internal resistance of the exhaust gas sensor or the electric heater is an initial internal resistance, the other correlation initial internal resistance, comparing the other correlation initial internal resistance with the other current internal resistance, and producing an abnormal condition judgement output in the case of a difference between the other correlation initial internal resistance and the other current internal resistance being greatly varied over a predetermined permissible value.

As a result of such arrangement, even if the internal resistance of the exhaust gas sensor and the electric heater has greatly changed due to an environmental temperature, it can be discriminated whether the current internal resistance has changed with age or has changed due to environmental temperature. An accurate correlation value can be calculated even though there might be a small amount of stored information, making it possible to reduce a memory capacity.

It is also preferable that the deterioration detector for an exhaust gas sensor of above arrangement according to the invention, in addition to the arrangement as described above, further comprises reset means for initializing information stored in each of data collection period judgement means, initial internal resistance correlation learning storage means and abnormal condition judgement means in response to a reset signal from outside.

As a result of such arrangement, even in the case of replacing the deteriorated exhaust gas sensor with a new one, detection of deterioration of such a new exhaust gas sensor can be conducted under the condition suitable for the new exhaust gas sensor.

A method for detecting deterioration of an exhaust gas sensor which is mounted on an exhaust pipe of an internal combustion engine for an automobile and arranged so as to control a temperature by an electric heater thereby detecting the deterioration of the exhaust gas sensor, comprising the steps of:

computing and storing an initial internal resistance of said exhaust gas sensor and said electric heater;

learning and storing a correlation in initial internal resistance between said exhaust gas sensor and said electric heater;

computing and storing a current internal resistance of said exhaust gas sensor and said electric heater;

calculating, on the assumption that either one of the current internal resistance of said exhaust gas sensor or said electric heater is an initial internal resistance based on said correlation learned and stored, the other logical internal resistance; and detecting a deterioration condition of said exhaust gas sensor and said electric heater by comparing the logical internal resistance with the other current internal resistance.

As a result, deterioration of the exhaust gas sensor as well as the abnormal condition of the electric heater can be detected, and a timing of replacement and repair of an integrally formed exhaust gas sensor and electric heater can be known.

Furthermore, even if the internal resistance of the exhaust gas sensor and the electric heater has greatly changed due to an environmental temperature, it can be discriminated whether the current internal resistance has changed with age or has changed due to environmental temperature. An accurate correlation value can be calculated even though there might be a small amount of stored information, making it possible to reduce a memory capacity.

DESCRIPTION OF THE PREFERRED EMBODIMENTS

Figure 1:
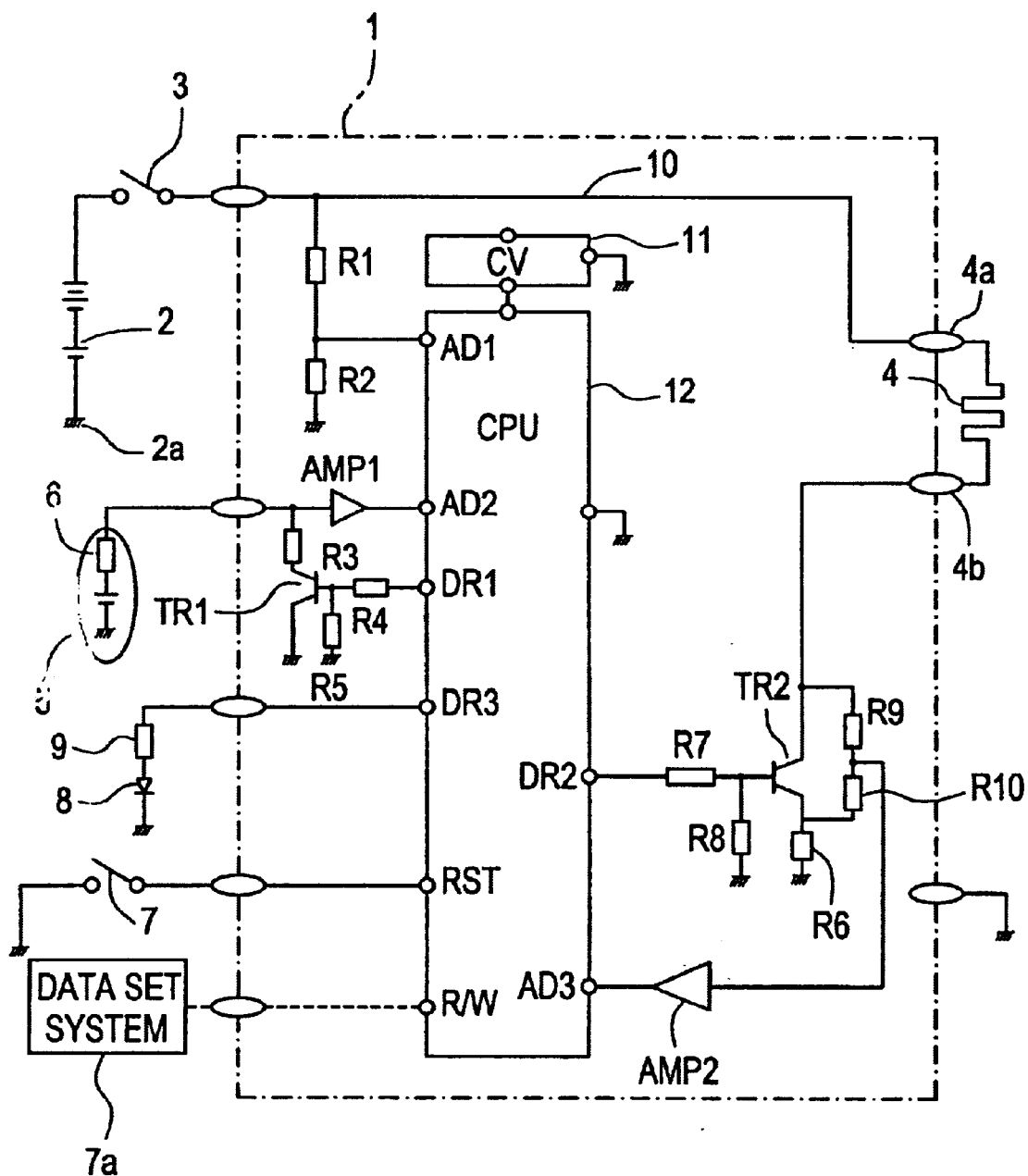
FIG. 1 is a circuit diagram of a deterioration detector for an exhaust gas sensor according to an embodiment of the present invention.
Figure 2:
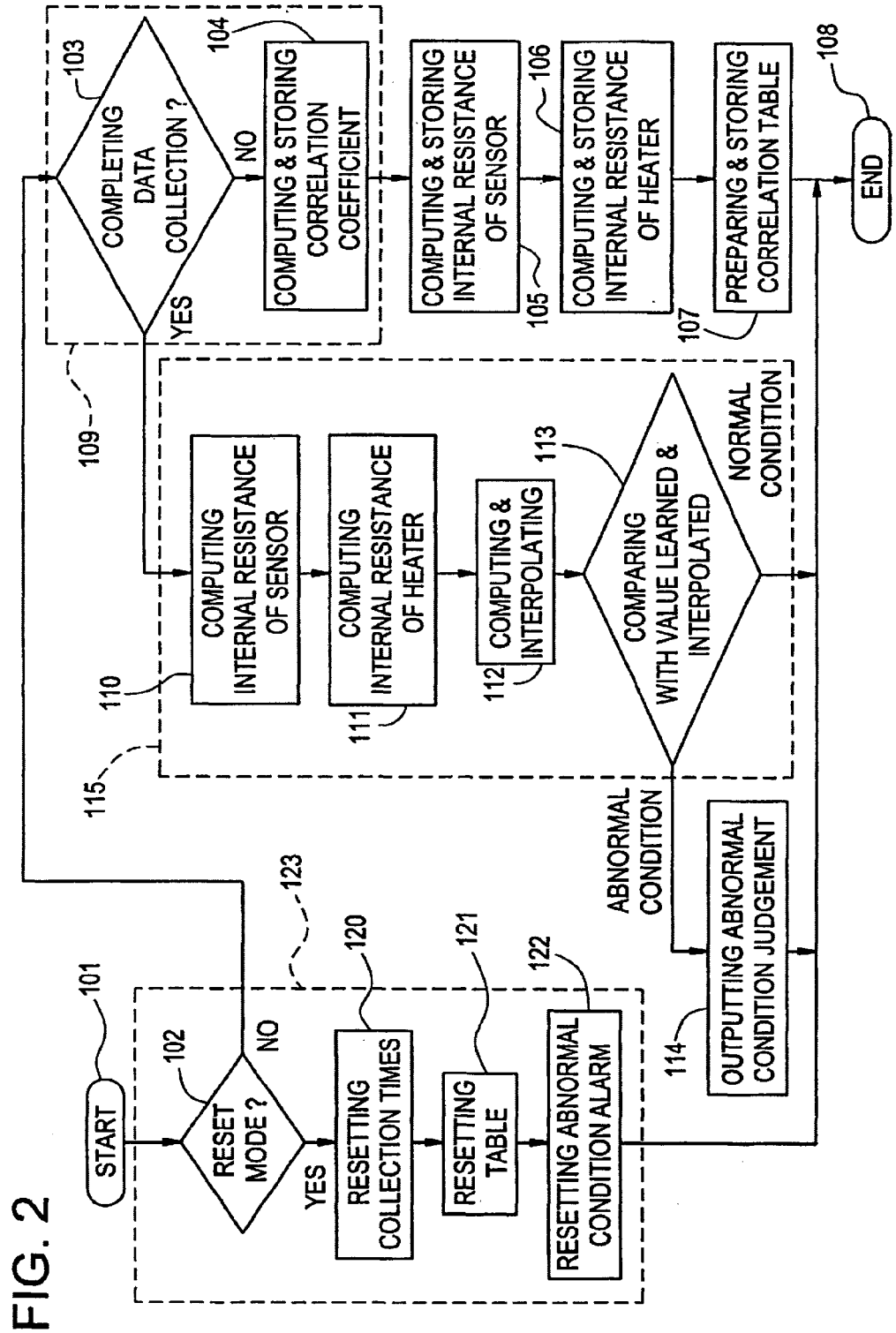
FIG. 2 is a flow chart showing an operation of the deterioration detector for the exhaust gas sensor according to the embodiment 1 of the invention.

A deterioration detector for an exhaust gas sensor according to an embodiment of the present invention is hereinafter described with reference to FIG. 1 and FIG. 2. FIG. 1 is an electric circuit diagram showing mainly an electric circuit of a deterioration detector for an exhaust gas sensor, and FIG. 2 is a flow chart showing an operation of the deterioration detector for an exhaust gas sensor arranged as shown in FIG. 1. In FIG. 1, reference numeral 1 is a deterioration detector to which an electrical power is supplied from a vehicle-mounted battery 2 of, for example, 12 volt via a power supply switch 3. Reference numeral 2a is a vehicle body to which a negative terminal of the vehicle-mounted battery 2 is connected. Numeral 4 is an electric heater that is electrically connected to the deterioration detector 1 via terminals 4a and 4b. Numeral 5 is an exhaust gas sensor that is electrically connected via a terminal to the deterioration detector 1 attached to an exhaust pipe of an internal combustion engine for an automobile. Numeral 6 is an internal resistance of the exhaust gas sensor 5, and the electric heater 4 and exhaust gas sensor 5 form an integral construction disposed adjacent to each other. Further, the electric heater 4 conducts temperature control of the exhaust gas sensor 5.

In addition, the deterioration detector 1 not only detects the deterioration of the exhaust gas sensor 5 and abnormal condition of the electric heater 4 but also is constructed to include various control functions such as the temperature control of the exhaust gas sensor 5 by the electric heater 4. Numeral 7 is a reset input switch that is connected to the deterioration detector 1. Numeral 7a is a data set system that is connected to the deterioration detector 1 and conducts various data setting upon delivery of a product and replacement of parts. Numeral 8 is an alarm display element such as light emitting diode that is connected to the deterioration detector 1 via a current limiting resistance 9.

Now, an internal arrangement of the deterioration detector 1 is hereinafter described.

Reference numeral 10 is a positive power supply wire that is connected to the vehicle-mounted battery 2 via the power supply switch 3. Numeral 11 is for generating a constant voltage output, for example, of DC 5V, and this constant voltage power supply system 11 is connected to the power supply wire 10. Numeral 12 is a microprocessor to which power is supplied from the constant power supply system 11. Further, one terminal 4a of the electric heater 4 is connected to the power supply wire 10.

Numerals R1 and R2 are voltage dividing resistances connected to the power supply wire 10. A voltage dividing value of the power supply voltage is connected to an input terminal AD1 of the microprocessor 12 for conversion from analog to digital thereby measuring the power supply voltage.

Numeral AMP 1 is an amplifier that is connected between the exhaust gas sensor 5 and an input terminal AD2 of the microprocessor 12 for conversion from analog to digital. Numeral TR1 is a transistor for connecting a load resistance R3 to the exhaust gas sensor 5. R4 is a base resistance that is connected to a pulse output terminal DR1 of the microprocessor 12 and drives the transistor TR1 to periodically turn ON/OFF. R5 is a ballast resistance in order to cause the transistor 1 to surely turn OFF.

Numeral TR2 is an open/close element such as a transistor, which is connected to the other terminal 4b of the electric heater 4. Numeral R6 is a current detection resistance that is connected in series to the open/close element TR2. Numeral R7 is a base resistance that is connected to a pulse output terminal DR2 of the microprocessor 12 and drives the open/close element TR2 to periodically turn ON/OFF. Numeral R8 is a ballast resistance that causes the open/close element TR2 to surely turn OFF.

Numerals R9 and R10 are voltage-dividing resistances that are connected putting the open/close element TR2 between them. Numeral MP2 is an amplifier for amplifying the divided voltage by the voltage dividing resistances and supplying the amplified voltage to a conversion input terminal AD3 of the microprocessor 12 for conversion from analog to digital. Distribution of resistance values such as voltage dividing resistances is as follow:

$$Rh \gg Re \; R9 \gg Rh \tag{1}$$

$$Rh{:}Re{\approx}R9{:}R10 \tag{2}$$

where: Rh shows an internal resistance of the electric heater 4, Re shows a resistance value of a current detection resistance R 6, R9 shows a resistance value of the voltage dividing resistance R9, and R10 shows a resistance value of the voltage dividing resistance R10 respectively.

Numeral DR3 is an output terminal of the microprocessor 12, and this microprocessor 12 drives the alarm display element 8 such as a light emitting diode via a current-limiting resistance 9. RST is an input terminal of the microprocessor 12 that is connected to the reset input switch 7. R/W is a terminal for serial communication of the microprocessor 12 that is connected to the data set system 7a, and the data set system 7a is connected to the terminal R/W for a serial communication only in a specific condition such as product delivery adjustment or parts replacement maintenance work.

Now, an operation of a deterioration detector for an exhaust gas sensor having an electric circuit arranged as shown in FIG. 1 is described with reference to a flow chart of FIG. 2.

In FIG. 2, Step 101 is an operation start step wherein an operation of a deterioration detector for an exhaust gas sensor starts just after a start-up of an engine of an automobile. After Step 101, a program proceeds to Step 102, wherein a reset mode judgement is conducted. In Step 102 (reset mode judgement step), it is judged to be a reset mode when the reset input switch 7 is ON, or a reset signal from the data set system 7a is input.

In Step 102, when it is judged not to be a reset mode, the program proceeds to Step 103 wherein a data collection completion is judged. In Step 103, it is judged whether a correlation coefficient computed and stored in later described Step 104 (correlation coefficient computing storage means) has reached to a predetermined value. The correlation coefficient is one data to be computed, renewed and come close to 1.0 sequentially, and data collection is judged completed when the value reaches not less than, for example, 0.7 (a predetermined value).

In Step 103, in the case that it is judged that data collection has not completed, the program proceeds to Step 104. In Step 104, computed and stored is a correlation coefficient of a pair of initial internal resistances of the exhaust gas sensor 5 versus the electric heater 4 to be stored in Step 107 later described wherein a correlation table of the initial internal resistances is prepared and stored (corresponding to initial internal resistance correlation learning storage means). The Step 104 is conducted when a sampling number of the initial internal resistances stored in later described Step 107 reaching not less than a predetermined number.

Step 109 corresponds to data collection period judgment means wherein Step 103 and Step 104 are included. As described above, in data collection period judgment means 109, based on the fact that a sampling number of an initial internal resistance of the exhaust gas sensor or the electric heater stored in initial internal resistance correlation learning storage means (corresponding to Step 107) is not less than a predetermined value and that a correlation coefficient not less than a predetermined value is secured, it is judged that data collection period has completed.

Then after Step 104, the program proceeds to Step 105 (initial internal resistance computing storage means). In Step 105, the internal resistance of the exhaust gas sensor is computed and stored. In Step 105, as shown in FIG. 1, when DR1 terminal of the microprocessor 12 comes to be a logical level L and a transistor TR1 is OFF, a generated voltage ES of the exhaust gas sensor 5 is directly input via AMP1 to an AD2 terminal of the microprocessor 12.

Then, when DR1 terminal comes to be a logical level H and the transistor TR1 is ON, a divided voltage E of the exhaust gas sensor 5 is input via AMP1 to AD2 terminal of the microprocessor 12.

Consequently, a resistance value RS of the internal resistance 6 of the exhaust gas sensor 5 is calculated by the following equation.

$$E{=}ES{\times}R3/(R3{+}RS) \therefore RS{=}R3{\times}(ES/E{-}1) \tag{3}$$

where: R3 is a resistance value of a load resistance R3.

In addition, although an actual value of resistance value RS of the internal resistance 6 of the exhaust gas sensor 5 is greatly different depending on the type of the exhaust gas sensor 5. For example, a linear-type oxygen concentration sensor has an extremely large temperature dependency such as 90Ω→30Ω corresponding to an atmosphere temperature 600° C. →700° C.

Subsequent to step 105, the program proceeds to step 106 (initial internal resistance computing storage means), in which the internal resistance of the electric heater 4 is computed and stored. In this Step 106, as shown in FIG. 1, when the DR2 terminal comes to be a logical level L and the open/close element TR2 is OFF, a divided voltage Eoff is input via AMP2 to AD3 terminal of the microprocessor 12. The divided voltage Eoff is expressed in the following equation.

$$Eoff{=}Eb{\times}(R6{+}R10)/(Rh{+}R9{+}R10{+}R6) \tag{4}$$

where: Eb is a power supply voltage which is measured by AD1 terminal of the microprocessor 12, R6 is a resistance value of the current detection resistance 6, R9 and R10 are resistance values of the voltage dividing resistances R9 and R10 respectively, and Rh is an internal resistance value of the electric heater 4.

A value of internal resistance Rh of the electric heater 4 calculated by equation(4), has a temperature dependency, for example, 21.5Ω→23Ω corresponding to an atmosphere temperature 600° C.→700° C.

Further, when DR2 terminal of the microprocessor 12 comes to be logical level H and the open/close element TR2 is ON, based on the fact that the divided voltage Eon is input to AD3 terminal of the microprocessor 12 via AMP2, an internal resistance of the electric heater 4 can be calculated by the following equation.

$$Eon \approx Eb \times R6/(Rh+R6) \quad (5)$$

However, there has been a temperature difference generated between a temperature of the electric heater 4 and an environmental temperature of the exhaust gas sensor 5, it is preferable to measure an internal resistance in the condition that the electric heater 4 has not been energized for not less than a predetermined period of time.

Further, in the case that an initial internal resistance of the exhaust gas sensor and electric heater which is newly sampled, computed and measured, is closely analogous to the initial internal resistance which is already learned and stored, in initial internal resistance correlation learning storage means (corresponding to Step 107), a value to be obtained by averaging the values of the initial internal resistance newly sampled and the initial internal resistance learned and stored, is renewed and stored. As a result, any useless proximate information is not stored so as to reduce a memory capacity, and an information amount to be referenced and read out is eliminated so that a high-speed processing of the microprocessor 12 can be conducted.

Then after Step 106, the program proceeds to Step 107, and in this Step 107, a correlation table of an initial internal resistance is prepared and stored (correlation table learning storage step). In Step 107, prepared is a table of an internal resistance of the electric heater 4 Rhi=F (Ti) versus an internal resistance of the exhaust gas sensor 5 Rsi=G(Ti) under various environmental temperature Ti (i=1, 2, ... n).

However, note that an environmental temperature Ti itself as a parameter is an unknown value and is not stored in the table, and it is a table just to know a direct correlation Rsi=H (Rhi), and above described letter F, G, H show correlation symbol.

Then after Step 107, the program proceeds to Step 108. Step 108 is an end step, and in which it is controlled so as to return to a start Step 101, for example a several minutes later.

Further, the internal resistances utilized in Step 105–Step 107 are those of the exhaust gas sensor 5 or the electric heater 4 in an initial condition (generally during several months after start the use), and it is required that initial values of the exhaust gas sensor 5 and the electric heater 4 themselves practically connected and used be learned due to a large fluctuation between products.

In the case that a completion of data collection is judged in Step 103, the program proceeds to Step 110. The Step 110 is a step wherein a current internal resistance Rs of the exhaust gas sensor 5 is calculated and stored, and the computing equation is as shown in the above equation (3).

Then after Step 111, the program proceeds to Step 112. The Step 112 is a computing interpolation step. In Step 112, by using a correlation learning value of an initial internal resistance Rsi=H (Rhi) prepared in Step 107, a logical internal resistance with respect to a current internal resistance Rh measured in Step 111 RsO=H (Rh).

However, when there is no value coincident to a current internal resistance Rh in Rhi (i=1, 2, ... n), by being linearly interpolated from internal resistances at two points Rhj and Rhk which are values above and below an internal resistance Rh ( Rhj <Rh <Rhk ), a logical internal resistance Rso with respect to an internal resistance Rh is calculated.

Then after Step 112, the program proceeds to Step 113. In Step 113, an internal resistance Rs (current resistance) computed and measured in Step 110 and a logical internal resistance RsO (initial resistance) calculated in Step 112 are compared with each other, and it is judged whether or not a difference value is greatly varied over a predetermined permissible variation value (a predetermined permissible value).

In Step 113, in case of judging that there has been a greater variation than a predetermined permissible value, the program proceeds to Step 114. The Step 114 is a step wherein an abnormal condition judgement output is generated, and it is arranged in such a manner that an alarm display element 8 is lighted by the abnormal condition judgement output.

In the case that either operation of Step 114 has completed or Step 113 judges the condition normal (no great variation), the program proceeds to Step 108, and it is externally controlled to proceed again to start Step 101a several minutes later. Numeral 115 is abnormal condition judgement means including Step 110–Step 113.

As described above, the abnormal condition judgment means 115 comprises a computing interpolation means (Step 112) for computing, on the assumption that either one of the current internal resistances of the exhaust gas sensor 5 or the electric heater 4 is an initial internal resistance, the other correlation initial internal resistance (logical internal resistance), compares the other correlation initial internal resistance with the other current internal resistance, and produces an abnormal condition judgement output in the case that a difference between the other correlation initial internal resistance and the other current internal resistance has varied greatly over a predetermined permissible value. Thus, when an abnormal condition is detected in either one or both of the exhaust gas sensor 5 and the electric heater 4, it is possible to know a timing to replace any integrally formed parts of the exhaust gas sensor 5 and the electric sensor 4.

Furthermore, in the case of Step 102 being a reset mode, the program proceeds to Step 120. In Step 120, a computed and stored value of a correlation coefficient obtained by correlation coefficient computing storage means (Step 104) within the data collection period judgement means 109, is reset and collection times are also reset.

Then after Step 120, the program proceeds to Step 121. The Step 121 is a table-reset step, and reset is a stored correlation value of an initial internal resistance learned and stored in correlation table creation storage step (Step 107) Then after Step 121, the program proceeds to Step 122. The Step 122 is an abnormal condition alarm reset step, and by resetting an abnormal condition judgement output produced in abnormal condition judgement output means (Step 114), the program proceeds to the end Step 108. Further, numeral 123 is reset means including Step 102, Step 120–Step 122.

As described above, reset means 123 initializes a storage information stored respectively in each reset means 123, data collection period judgement means 109, initial internal resistance correlation learning storage means (corresponding to Step 107) and abnormal condition judgement means 115, in response to a reset signal from the outside. As a result, based on the fact that the integrally formed exhaust gas sensor 5 and electric heater 4 are performed after replacement of parts, it becomes possible to detect deterioration corresponding to a characteristic of a newly incorporated exhaust gas sensor 5 and electric heater 4.

As described above, a deterioration detector for an exhaust gas sensor according to the invention comprises: initial internal resistance correlation learning storage means (corresponding to Step 107) for sequentially sampling, calculating and storing an initial internal resistance of the exhaust gas sensor 5 and the electric heater 4; data collection period judgement means 109 for determining a period of time of sampling the initial internal resistance; and abnormal condition judgement means 115 for computing and storing a current internal resistance of the exhaust gas sensor 5 and the electric heater 4 after a predetermined period of time following a start-up of an internal combustion engine for an automobile, and for conducting an abnormal condition processing in the case of the current internal resistance being greatly varied over a predetermined permissible value by comparing the current internal resistance with the initial internal resistance. As a result of employing such arrangement, observation of change with age of the exhaust gas sensor 5 enables the detection of deterioration of the exhaust gas sensor 5. Furthermore, even if an abnormal condition such as a short circuit or an opened circuit in the electric heater 4 should take place, abnormal condition output is generated, and abnormal condition of the electric heater 4 can be also detected.

In addition, an exhaust gas sensor shown in FIG. 1 is an example of a non-linear exhaust gas sensor, however it is preferable to employ such a type of exhaust gas sensor as to measure an internal resistance by utilizing a linear-type exhaust gas sensor having two or three terminals. It is also preferable that an integrated circuit parts such as those for obtaining a detection oxygen voltage signal or a voltage signal in proportion to the internal resistance be incorporated outside the microprocessor 12.

Additionally, in the foregoing description of FIG. 2, a correlation learning value of the initial internal resistance learned and stored in Step 107 is obtained by calculating an internal resistance Rsi of the exhaust gas sensor 5 employing an internal resistance Rhi of the electric heater 4 as a reference, however either of the mentioned internal resistances may be an available reference.

What is claimed is:

1. A deterioration detector for an exhaust gas sensor that is mounted on an exhaust pipe of an internal combustion engine for an automobile and is provided so as to control a temperature control of said exhaust gas sensor by an electric heater thereby detecting deterioration of the exhaust gas sensor comprising:

initial internal resistance correlation learning storage means for sequentially sampling, comparing, computing and storing an initial internal resistance of said exhaust gas sensor and said electric heater, as well as learning and storing a correlation between the initial internal resistance of said exhaust gas sensor and the initial internal resistance of said electric heater;

data collection period judgment means for determining a period of sampling said initial internal resistance of said exhaust gas sensor and said electric heater; and abnormal condition judgment means for computing and storing a current internal resistance of said exhaust gas sensor and said electric heater after a predetermined period of time of an operation start of said internal combustion engine for an automobile, for judging that said current internal resistance of said exhaust gas sensor or said electric heater is less than or greater than predetermined permissible values by comparing said current internal resistance of said exhaust gas sensor and said electric heater with said initial internal resistance of said exhaust gas sensor and said electric heater, respectively, thereby conducting a processing for an abnormal condition.

2. The deterioration detector according to claim 1, wherein, in the case that an initial internal resistance of the exhaust gas sensor and the electric heater which is newly sampled, computed and measured, is substantially identical to the initial internal resistance of said exhaust gas sensor and said electric heater already learned and stored, the initial internal resistance correlation learning storage means averages the values of said initial internal resistance of said exhaust gas sensor and said electric heater newly sampled with that of said initial internal resistance of said exhaust gas sensor and said electric heater learned and stored, respectively, and stores the averaged values in place of the initial internal resistance of said exhaust gas sensor and said electric heater already learned and stored.

3. The deterioration detector according to claim 1, wherein the data collection period judgment means judges a completion of the data collection period based on the fact that a sampling number of the initial internal resistance of the exhaust gas sensor or the electric heater stored in initial internal resistance correlation learning storage means, is not less than a predetermined number and a correlation coefficient not less than a predetermined value is obtained.

4. The deterioration detector according to claim 1, wherein the abnormal condition judgment means comprises computing interpolation means for computing a logical initial internal resistance, by selecting either one of the current internal resistance of the exhaust gas sensor or the electric heater to be a selected initial internal resistance, the selected initial internal resistance and the already learned and stored initial internal resistances are used to compute the logical initial internal resistance through interpolation, and then comparing the logical initial internal resistance with the non-selected current internal resistance, and producing an abnormal condition judgment output in the case of a difference between the logical initial internal resistance and the non-selected current internal resistance being within a predetermined permissible range of values.

5. The deterioration detector according to claim 1, further comprising reset means for initializing information stored in each of data collection period judgment means, initial internal resistance correlation learning storage means and abnormal condition judgment means in response to a reset signal.

6. A method for detecting deterioration of an exhaust gas sensor which is mounted on an exhaust pipe of an internal combustion engine for an automobile and provided so as to control a temperature control of the exhaust gas sensor by an electric heater thereby detecting the deterioration of the exhaust gas sensor, comprising the steps of:

computing and storing an initial internal resistance of said exhaust gas sensor and said electric heater;

learning and storing a correlation between the initial internal resistance of said exhaust gas sensor and the initial internal resistance of said electric heater;

computing and storing a current internal resistance of said exhaust gas sensor and said electric hearer;

computing a logical initial internal resistance, by selecting either one of the current internal resistance of said exhaust gas sensor or said electric heater to be a selected initial internal resistance, the selected initial internal resistance and the already learned and stored initial internal resistances are used to compute the logical initial internal resistance through interpolation; and detecting a deterioration condition of said exhaust gas sensor and said electric heater by comparing the logical initial internal resistance with the non-selected one of the current internal resistance of said exhaust gas sensor or said electric heater.

* * * * *